(12) United States Patent
Pilcher et al.

(10) Patent No.: US 7,267,673 B2
(45) Date of Patent: Sep. 11, 2007

(54) SYSTEM FOR TREATMENT OF ACNE SKIN CONDITION USING A NARROW BAND LIGHT SOURCE

(75) Inventors: Kenneth A. Pilcher, Seattle, WA (US); Robert E. Akridge, Seattle, WA (US); David Giuliani, Mercer Island, WA (US); Ward E. Harris, Bellevue, WA (US); Stephen M. Meginniss, Seattle, WA (US)

(73) Assignee: Pacific Biosciences Laboratories, Inc., Bellevue, WA (US)

( * ) Notice: Subject to any disclaimer, the term of this patent is extended or adjusted under 35 U.S.C. 154(b) by 115 days.

(21) Appl. No.: 10/317,965

(22) Filed: Dec. 12, 2002

(65) Prior Publication Data

US 2004/0116913 A1    Jun. 17, 2004

(51) Int. Cl.
*A61B 18/18*    (2006.01)
(52) U.S. Cl. ............... 606/9; 606/3; 606/10; 607/88
(58) Field of Classification Search .............. 606/3, 606/9–11, 13, 16–19; 607/88–91, 94; 128/898
See application file for complete search history.

(56) References Cited

U.S. PATENT DOCUMENTS

| | | | | |
|---|---|---|---|---|
| 4,930,504 | A * | 6/1990 | Diamantopoulos et al. ... | 607/88 |
| 5,464,436 | A * | 11/1995 | Smith ........................... | 607/89 |
| 5,616,140 | A * | 4/1997 | Prescott ........................ | 606/10 |
| 5,913,883 | A * | 6/1999 | Alexander et al. ............ | 607/88 |
| 6,096,066 | A * | 8/2000 | Chen et al. .................... | 607/88 |
| 6,443,978 | B1 * | 9/2002 | Zharov ......................... | 607/91 |
| 6,596,016 | B1 * | 7/2003 | Vreman et al. ............... | 607/88 |
| 6,835,202 | B2 * | 12/2004 | Harth et al. ................... | 607/91 |
| 6,887,260 | B1 * | 5/2005 | McDaniel ..................... | 607/91 |
| 6,981,970 | B2 * | 1/2006 | Karni ............................ | 606/9 |
| 7,066,941 | B2 * | 6/2006 | Perricone ..................... | 606/88 |
| 2004/0044384 | A1 * | 3/2004 | Leber et al. .................. | 607/88 |

* cited by examiner

*Primary Examiner*—A. Farah
(74) *Attorney, Agent, or Firm*—Jensen & Puntigam, P.S.

(57) ABSTRACT

The acne treatment devices use an array of LEDs, which emit monochromatic light substantially at a wavelength of 405 nanometers, which is coincident with the peak absorbance of light by acne porphyrins. The emitted light is directed from the light source to an acne area of the skin. The device can either be hand-held, with the LEDs mounted on a handle portion, or an LED can be mounted on a patch-like mounting element, which is adapted to be secured to the skin for longer exposure at less intensity.

4 Claims, 4 Drawing Sheets

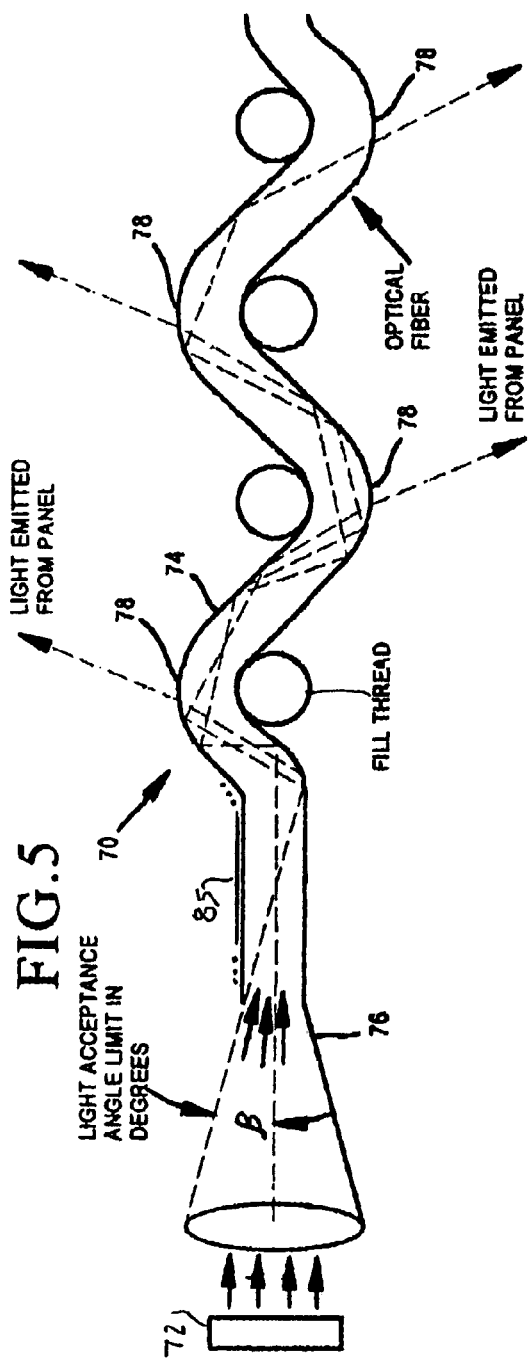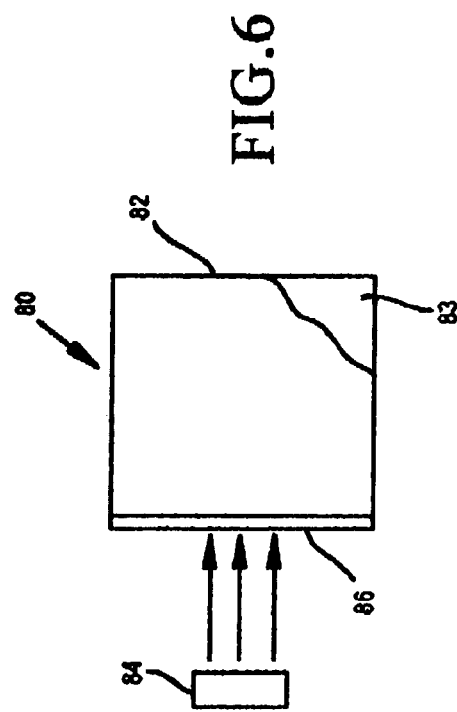

SYSTEM FOR TREATMENT OF ACNE SKIN CONDITION USING A NARROW BAND LIGHT SOURCE

TECHNICAL FIELD

This invention relates generally to the treatment of acne (skin condition) in humans, and more specifically concerns the treatment of such skin condition using light.

BACKGROUND OF THE INVENTION

There are many well-known bacteria which cause various medical conditions. The bacteria P. acnes has been indicated to be responsible for the acne skin condition in humans, generally known as acne vulgaris, which is the most commonly treated skin condition in the United States. Acne has long been problematic for young adults, but older adults are often affected as well. Effective acne treatment is emphasized, particularly for young people, because of the often long-term consequences, both physical and emotional, which occur due to the unsightly acne skin condition.

Because acne primarily occurs during adolescence, when self-image is being formed, even a mild case can have a profoundly negative effect on the psychosocial development of the individual, including school performance. Further, a moderate to severe acne condition, with its usual long-term scarring effects, can cause disfigurement, often significant, that persists throughout lifer which can affect career choice and employment opportunities.

While, as indicated above, acne occurs most frequently in young (adolescent) adults, it is not always resolved by the end of the teenage years and may persist into the 40's for certain individuals. In some cases, the onset of acne may not occur until the mid-20's.

For all the above reasons, it is important to recognize that acne is a significant medical condition, and that it affects a significant part of the population, and many age groups.

Acne treatment includes diet restrictions, antibiotics (both oral and topical), as well as exposure to sunlight and other light sources. Retinoids and hormonal manipulation treatment are also used. Diet restrictions are typically problematic, with unpredictable results. Oral antibiotics have been successfully used to treatment acne, but can have disadvantages, including yeast vaginitis, gastrointestinal side effects and photosensitivity. Retinoids are not advised for women of child-bearing potential and often cause xerosis (dry skin), erythema, cheilitis, conjunctival irritation and alopecia, while hormonal therapy expose the patient to risk of thromboembolism, feminization (in men) and other undesirable effects. Topical antibiotic applications are also used for acne treatment, including retinoids, benzoyl peroxide, salicylic acid and antibiotics. Each of these has their specific undesirable side effects, including undesirable skin surface reactions in some cases.

Light therapy has also been used for acne treatment, including exposure to sunlight. While ultraviolet light has been used in the past in clinical situations to treat acne, such treatment is no longer recommended because of the risk of skin cancer. Existing clinical devices using ultraviolet light are expensive and sufficiently risky that they must be used by medical professionals. The effect of light treatments has in some cases been enhanced by the use of selected photosensitive chemicals. However, such therapy, using a combination of light and selected chemicals, is often uncomfortable, causing stinging, erythema, epidermal exfoliation and hypersensitivity.

New developments in acne treatment involve narrow band light. These developments are illustrated in the following patents and patent applications: U.S. Pat. No. 5,549,660 to Mendes et al uses a light source with a wavelength of 660 nanometers. This, however, has not proven to be particularly effective. Patent Applications No. 20010028227 and 20010023363 to Lys and Harth teach, respectively, the use of light-emitting diodes (LEDs) and 400 watt metal halide lamps which are filtered to emit light in the 407-420 nanometer wavelength range, which has been shown to be effective against certain acne bacteria. The lamps are used to illuminate the entire face. They are large and expensive. LEDs on the other hand are small (on the order of 0.100") and relatively low cost.

Further, metal halide lamps are inefficient relative to power required and create significant problems in the skin area being treated. A clinical setting and supervision are required. In contrast, LEDs have efficiencies of 15-20%.

There is no effective home use treatment for acne using light. It is hence desirable that an effective treatment of acne using light be developed which is safe, inexpensive and simple to use at home.

SUMMARY OF THE INVENTION

Accordingly, the present invention is a hand-held apparatus for treatment of skin acne, which comprises: a handle member which is configured to be suitable for grasping by an individual; a monochromatic source of light with a wavelength which is substantially coincident with the maximum absorbance of light by acne porphyrins; and a light-conducting member which directs the light emitted by the light source over a relatively small, defined area at an output end thereof, wherein the output end can be conveniently applied to an acne area on the skin of a user, the apparatus being otherwise configured and arranged to permit a user to conveniently use the apparatus for treatment of acne.

Another embodiment of the present invention is an article for treatment of skin acne, comprising: a flexible mounting element adapted to be suitable for placement on and attachment to the skin of a user in the vicinity of acne to be treated; and a monochromatic source of light mounted on the mounting element, with a wavelength which is substantially coincident with the maximum absorbance of light by acne porphyrins, the source of light being mounted such that light is directed to the acne when the mounting element is properly placed on the user's skin.

Another embodiment is an article for treatment of acne, comprising: a woven fabric member adapted for attachment to the surface of the skin; and a monochromatic source of light, applied to an edge portion of the fabric member, at a wavelength which is substantially coincident with the maximum absorbance of light by acne porphyrins, wherein the fabric member fibers are configured such that light escapes at bend points in the weave of the fabric, resulting in a relatively uniform distribution of light over the area of the patch.

Another embodiment of the invention is an article for treatment of acne, comprising: a molded sheet adapted for attachment to the skin of a user; and a monochromatic source of light, applied to an edge portion of the sheet, at a wavelength which is substantially coincident with the maximum absorbance of light by acne porphyrins, wherein the surface of the plastic sheet in contact with the skin is molded into a shallow arrangement of impressions that result in the light within the sheet from the light source being emitted perpendicularly to the surface of the sheet and directed toward the skin, wherein the output of light from the sheet is relatively constant over the entire surface of the sheet.

BRIEF DESCRIPTION OF THE DRAWING

FIGS. 4A, 4B, 5 and 6 show other embodiments using light to treat acne embodying the principles of the present invention.

BEST MODE FOR CARRYING OUT THE INVENTION

As indicated above, both natural sunlight and light from particular sources, including a metal halide lamp with a filter to provide light with a selected wavelength have been used to treat acne vulgaris (hereafter referred to as acne). Filtered light sources are also used to diagnose acne. For some time, the reasons for the success of sunlight were not clearly understood. Further, sunlight treatment was and is accompanied by the undesirable effects of burning and even skin deterioration and cancer, caused by the ultraviolet (UV) wavelengths in sunlight.

Acne is a rather complicated skin condition, which involves basically three skin processes or stages. The first process or stage in the development of acne is formation of a microcomedone (plug), which is a microscopic concentration of keratinocytes, sebum and colonies of bacteria formed in the follicular infundibulum (skin pore). The microcomedone then increases in size, with increased adherence of cornified cells, resulting in closure of the infundibulum (pore), which in turn promotes a microaerobic environment.

The second process/stage is known as seborrhea, involving an increased rate of sebum production, which supplies nutrients for the P.acnes bacteria. This occurs within a pilosebaceous unit area confined by the closed comedone resulting from the first process.

In the third process, microbial colonization occurs in the resulting sebum-rich environment. When the infundibulum becomes blocked by the microcomedone, the balance within the pilo sebaceous unit is upset; if the conditions of pH and oxygen are correct within the closed comedone, the bacteria grows in number and produces a pathogenic effect, resulting ultimately in an acne lesion (pimple). This process can include damage to the follicular walls and extrusion of lipids.

It has been discovered that the P.acnes bacteria include certain porphyrins, which, upon absorbing light in the visible spectrum, in the presence of oxygen, results in the exciting of an electron in its structure. The excited electron then breaks an adjacent oxygen molecule into singlet oxygen free radicals. The reactive oxygen initiates a series of chemical reactions, which ends in the killing of the bacteria.

As discussed briefly above, previous light sources used in the treatment of acne have suffered from a number of undesirable side effects. Specifically, these include the presence of secondary wavelengths in the emitted light, relatively poor efficiency, in terms of input power requirements of broadband light sources, the expense and complexity of filtering broadband light when only a narrow band is actually to be used, significant heat generation by the light devices, requiring specialized, expensive equipment and complicated optic systems in order to limit the exposure of the skin. Exposure time is excessive for practical home use. All of the previous light treatment devices have required the supervision of a medical professional.

Figure 1:
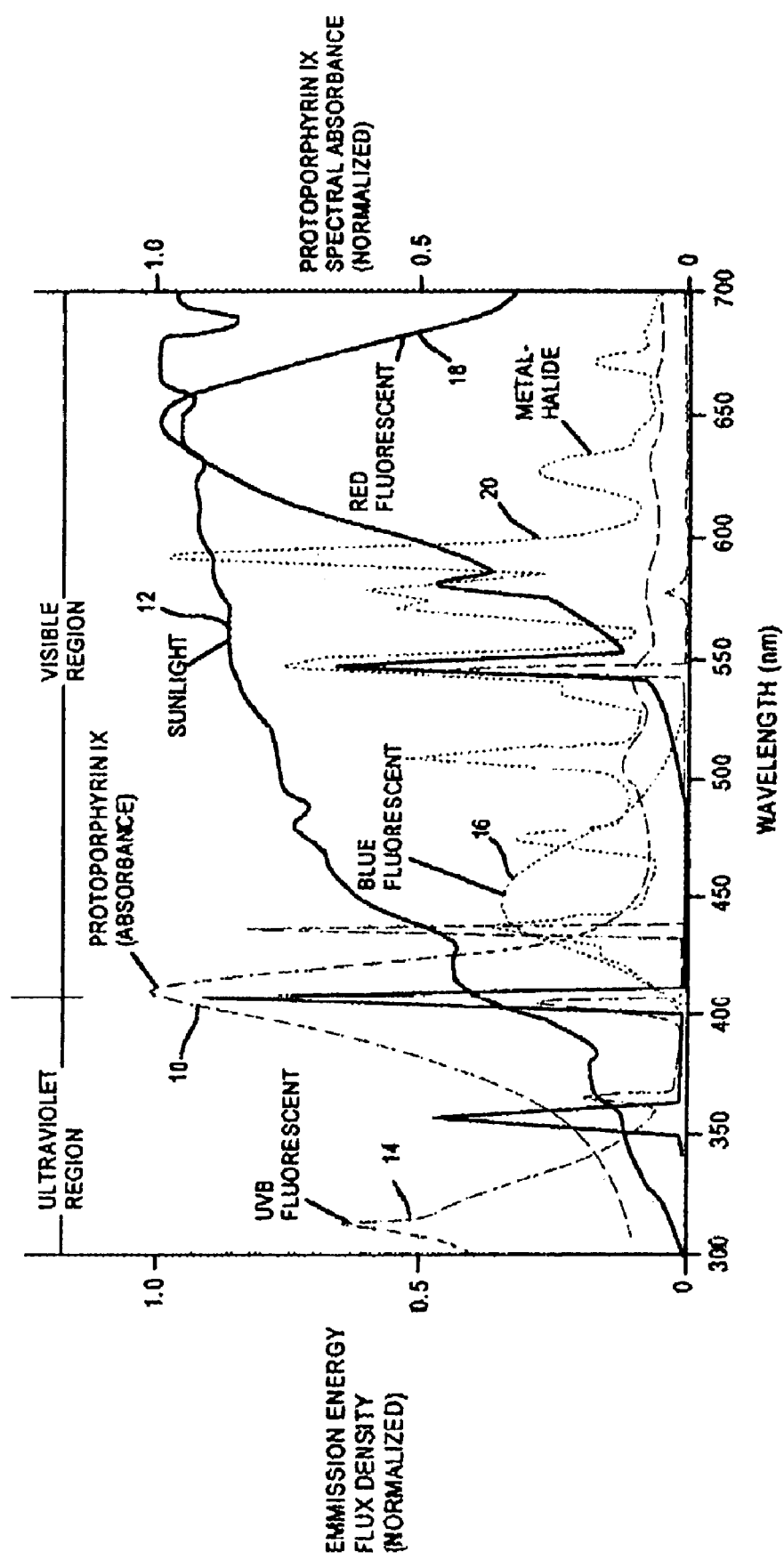
FIG. 1 is a diagram showing the emission spectra of sunlight and other traditional phototherapy light sources relative to the absorption spectrum of P.acnes porphyrins.

In the present invention, a light source is used which actually produces, without filtering, narrow band light which closely approximates that of the primary visible light absorption characteristic of the porphyrins in P.acnes bacteria, i.e. an absorbance spectra peak of 409 nanometers (violet). The light produced by the apparatus of the present invention stimulates the P.acnes porphyrins with light at that wavelength. FIG. 1 illustrates generally the peak absorbance of the porphyrins and the spectra of various light sources. The absorbance peak of P.acnes porphyrins at 409 nanometers is referred to at 10, while sunlight emission spectrum is referred to at 12. Individual ultraviolet, blue fluorescent and red fluorescent light sources are referred to at 14, 16 and 18, respectively, while the spectrum of a metal halide source is referred to at 20. Sunlight radiation, particularly in the ultraviolet bands, is associated with skin deterioration and cancer, while the red and blue fluorescent bulbs and metal halide lights have relatively little wavelength content at the key wavelength of P.acnes porphyrins, making them highly inefficient for treatment of acne.

Figure 2:
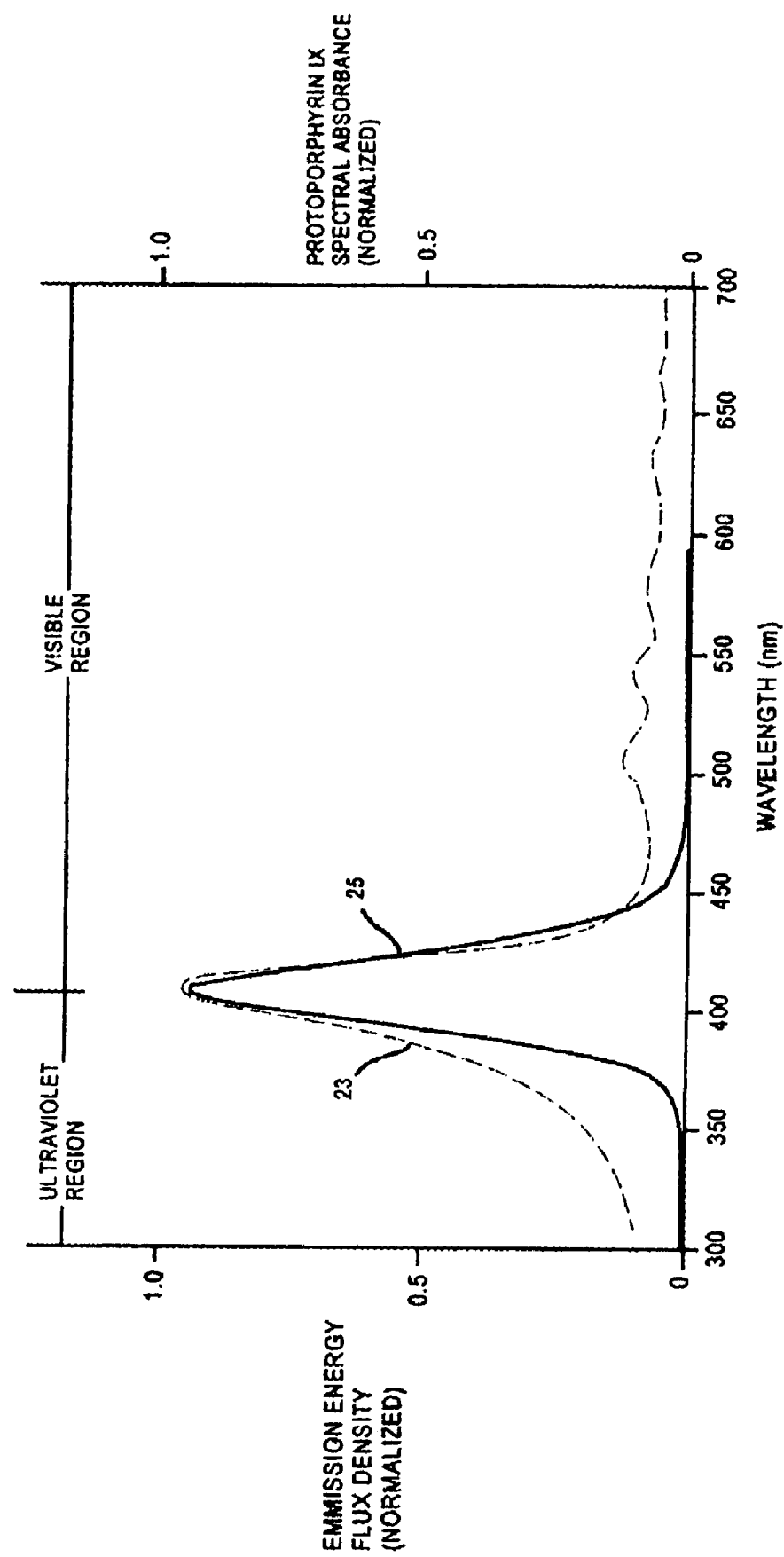
FIG. 2 is a diagram showing in more detail a portion of the diagram of FIG. 1, comparing the emission spectrum of a violet blue LED (405 nanometers wave length) with the absorbance spectrum of P.acnes porphyrin.

The present invention includes a light source, which emits light in a narrow band which closely approximates the peak absorbance wavelength of the P.acnes porphyrins, 405 nanometers. FIG. 2 shows the absorbance spectra 23 of a typical p.acnes porphyrin relative to the emission spectra 25 of the light source used in the invention. The light source is unfiltered, so there is no loss of light energy. The present invention is configured and adapted for convenient, economical and safe home use, without the aid of a medical professional.

Figure 3A:
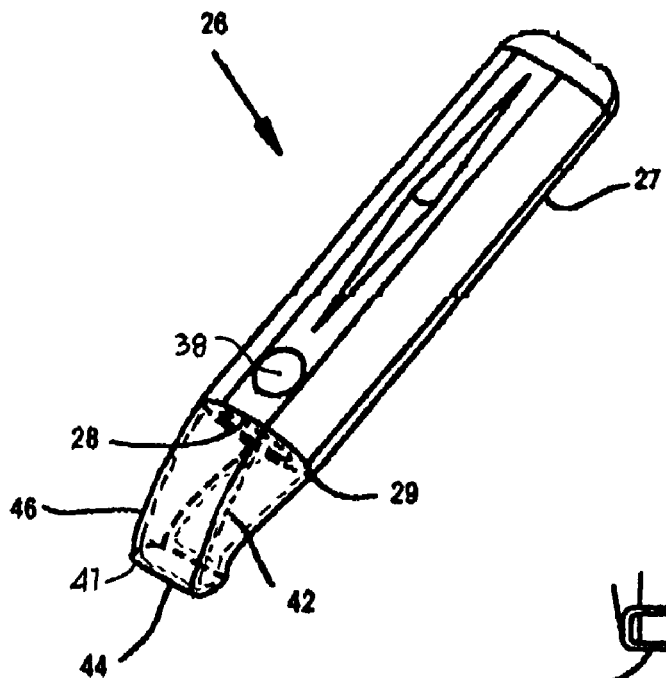
FIGS. 3A, 3B and 3C show a hand-held device of the present invention for treatment of acne.
Figure 3B:
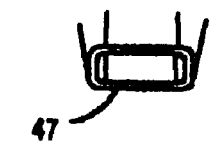
Figure 3C:

The first embodiment of the invention is shown in FIG. 3. It is a hand-held apparatus appropriate for short-term light exposure, suitable for home use. The apparatus, referred to generally at 26, includes a handle 27 and a monochromatic light source 28, which is mounted at the forward end 29 of the handle and emits radiation at the desired wavelength of 405 nanometers. In the embodiment shown, the monochromatic light source is a solid-state light source, in particular an LED or LED array or laser diode. Alternatively, the light source could be an organic LED or electroluminescent element or other monochromatic light source. More specifically in the embodiment shown, light source 28 is a 4×4 array of 405 nanometer LEDs, which is mounted on a common interconnecting substrate. The array provides greater intensity and/or increased coverage relative to a single LED. Handle 27 in the embodiment shown is generally rectangular, sized and configured for convenient handheld use, curved at the corners and along the longitudinal edges for convenience of the user. The LED array is driven by a constant current circuit powered by a battery producing approximately 15-30 mA and preferably 20 mA current for each LED. The constant current circuit and battery are both located in the handle.

Each LED in the array emits relatively intense light, designed for site-specific treatment of a single acne lesion or for moving across the skin in the treatment of a larger area. The intensity of the emitted light is approximately 20 milliwatts per square centimeter or less, which is effective but significantly less than sunlight. The emitted light is approximately 40 times more efficient in stimulating the *p.acnes* porphyrins than sunlight. The exposure time using the apparatus of FIG. 3 will typically be a matter of a few minutes, once or twice a day. A conventional battery is typically used in the apparatus, preferably rechargeable. The device is activated by an on/off button 38.

Extending from the forward end 29 of handle 27 is an optical light directing pipe or "scrambler" 42, which conducts the emitted light from the LED light source 28 to the surface of the skin being treated. The light conductor 42 is a transparent body which can be made from acrylic and coated internally with a white plastic which includes titanium dioxide so that light reflects and refracts and is radiated back into the interior of the conductor, exiting at the outlet port 44 thereof onto the skin of the user.

The apparatus 26 may also include optical devices such as lenses (not shown), which will further focus the emitted light onto a desired spot size.

Extending closely around the light conductor 42 is an optional removable light spreader 46. It terminates in a free end 47, which is in approximately the same plane as the conductor 42. The end of spreader 46 through which the emitted light comes can have various configurations, including rectangular (47), circular (47a), elliptical or other configurations, depending upon the desired configuration of the radiation.

Handle 27 can also house additional electronic controls for the device. These can include a circuit for temporary disabling of the apparatus if it is not in a correct position for safe use, such as in contact with a surface; a timing element which controls the operation of the device to ensure that the exposure time is correct, an audible or visual indicator for indicating to the user when the desired exposure time has expired, and an indicator element which indicates battery charge status.

The device 26 of FIG. 3 is advantageous because of the use of the monochromatic LEDs, which have the advantage of low heat generation and efficient production of only the desired light wavelength. The device 26 is thus a convenient, hand-held device, which is conveniently usable at home by non-medical personnel.

Figure 4A:
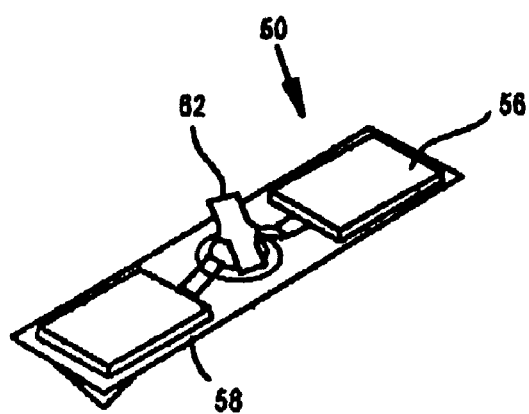
Figure 4B:
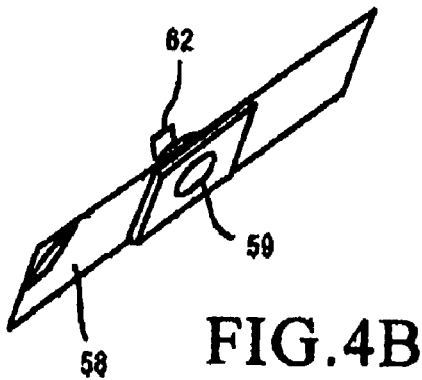

FIGS. 4A and 4B show an embodiment, which is attachable directly to the skin, and designed to be used for longer periods of time than would be convenient or comfortable for the hand-held device of FIG. 3. The device 50 is designed for spot treatment of an area, i.e. one to five centimeters across. The light source (not shown specifically) is integral to the device and comprises a single 405 nanometer LED driven by a control circuit on a common interconnecting substrate with batteries 56, all mounted on an adhesive plastic strip 58. The adhesive plastic strip 58 is designed to be attached to the skin for the length of the treatment. Other attachment means besides adhesive, however, can be used. These could include Velcro® strips, or a mask or headband element of some kind. The LED emits relatively low intensity light, less than 5 milliwatts per centimeter, through a light outlet port 59.

The apparatus 50 includes a convex lens (not shown), which encapsulates the LED and produces a small air gap, on the order of 2-5 millimeters, between the light source and the skin. This spreads the light and directs it through port 59 to a small spot on the skin, desirably one centimeter or so in diameter. A switch element 62 is provided which can be conveniently turned by the user to turn the LED on and off. When the switch is in the on position, the LED is activated and the light is provided directly onto the acne lesion until the battery is discharged.

Alternatively, the battery and the drive circuit could be positioned in a module, which is separate from the unit 50, with wires connecting the drive circuit and battery to the LED on the unit. Additional electronics could be provided for indicating expiration of exposure times and/or battery charge status or other information. The device/unit of FIGS. 4A and 4B is designed for longer-term exposure (a few hours) of a small area at low intensity. The attachment member results in the treatment being "hands free".

Another embodiment for attachment to the skin of a user over a large treatment area (greater than 100 cm$^2$) is shown in FIG. 5. A device 70 produces a pattern of light emission at relatively low intensity (less than 5 milliwatts per centimeter squared). The exposure time for the treatment area will be on the order of a few hours. Device 70 includes a monochromatic light source 72 and a woven fabric patch 74 of optical fiber. The fabric is sufficiently flexible that the entire patch will conform to the shape of the skin treatment area. The patch may also be preformed to match the contour of a particular part of the face or body.

The light from LED 72 is applied to the fiber bundle 76 of the patch over a specified acceptance angle. Light escapes from the fiber patch at the bends 78 in the weave, as shown in FIG. 5, which results in a relatively uniform distribution of light over the surface of the fabric. A reflective element or layer 85 redirects any light escaping from the upper side of the patch back toward the skin. The light source, battery and drive circuit can be mounted on the fabric patch, but alternatively can be mounted on a module, which is coupled to the fabric. The fabric patch can be attached to the skin for "hands-free" treatment by various means including adhesives, etc.

FIG. 6 shows another "patch" embodiment designed for attachment to the skin for treatment of a relatively large area, with low intensity (less than 5 mW/cm$^2$). Patch 80 includes a molded plastic sheet 82 and a lower adhesive layer 83, which secures the device to the skin temporarily and is transmissive for the emitted light. The sheet 82 is activated by a light source 84 at an edge 86 thereof. The patch 80 is sufficiently flexible to conform to the shape of the treatment area. Additionally, the patch may be preformed to match the contour of a particular part of the face or body.

The lower surface of layer 83 in contact with the skin is molded such that it has a shallow arrangement of impressions, which cause the light within the sheet from the monochromatic light source to be emitted perpendicular to its surface and toward the skin. The pattern of the impressions is such that the output of light is relatively constant over the entire surface area of the sheet. A reflective element 85 redirects any light escaping from the upper side of the patch back toward the skin.

The devices of FIGS. 4A, 4B, 5 and 6 are all low intensity, longer-term (a few hours) treatment devices. They are all secured or attached to the skin in some way, either by adhesives, a strap or other means, so that the devices can be used essentially hands-free for the recommended treatment time.

Hence, the present invention is directed toward an efficient, safe treatment for acne using light, in which a monochromatic source of light having a specific wavelength is used, which is substantially coincident with the peak absorbance of the porphyrins present in the *p.acnes* bacteria. The light is produced by an LED or other inherently monochromatic light source and positioned in either a hand-held device or patch-like devices and controlled so that the devices are convenient, safe and reliable to be used by a non-medical professional at home.

Although a preferred embodiment of the invention has been described for purposes of illustration, it should be understood that various changes, modification and substitutions may be incorporated in the embodiment without departing from the spirit of the invention, which is defined by the claims, which follow.

What is claimed:

1. An article for treatment of skin acne, comprising:
   a woven fabric member adapted for attachment to the surface of the skin; and
   a monochromatic source of light, applied to an edge portion of the fabric member, at a wavelength which is substantially coincident with the maximum absorbance of light by acne porphyrins, wherein substantially all of the monochromatic light has a single wavelength, wherein the fabric member fibers are configured such that light escapes at bend points in the weave of the fabric, resulting in a relatively uniform distribution of light over the area of the patch.

2. An article of claim 1, wherein the light source is an LED with a wavelength of emitted light of approximately 405 nanometers.

3. An article for treatment of skin acne, comprising:
   a molded sheet adapted for attachment to the skin of the user; and
   a monochromatic source of light, applied to an edge portion of the sheet, at a wavelength which is substantially coincident with the maximum absorbance of light by acne porphyrins, wherein substantially all of the monochromatic light has a single wavelength, wherein the surface of the sheet in contact with the skin is molded into a shallow arrangement of impressions that result in the light within the sheet from the light source being emitted perpendicularly to the surface of the sheet and directed toward the skin, wherein the output of light from the sheet is relatively constant over the entire surface of the sheet.

4. An article of claim 3, wherein the light source is an LED with a wavelength of substantially 405 nanometers.

* * * * *